(12) United States Patent
Noetzli et al.

(10) Patent No.: US 7,481,842 B2
(45) Date of Patent: Jan. 27, 2009

(54) IMPLANT SYSTEM

(75) Inventors: Hubert Noetzli, Liebefeld (CH); Roland Willi, Neftenbach (CH)

(73) Assignee: Zimmer, GmbH, Winterthur (CH)

( * ) Notice: Subject to any disclaimer, the term of this patent is extended or adjusted under 35 U.S.C. 154(b) by 294 days.

(21) Appl. No.: 11/180,368

(22) Filed: Jul. 12, 2005

(65) Prior Publication Data

US 2006/0012127 A1    Jan. 19, 2006

(30) Foreign Application Priority Data

Jul. 19, 2004    (EP) .................................. 04016985

(51) Int. Cl.
*A61F 2/36*    (2006.01)
*A61F 5/00*    (2006.01)
(52) U.S. Cl. ................ 623/23.31; 606/86 R; 623/23.26
(58) Field of Classification Search ............. 623/22.11, 623/22.12, 23.15, 23.23, 23.26, 23.35, 23.29–23.31; 606/79, 86, 80, 89, 85, 87, 86 R
See application file for complete search history.

(56) References Cited

U.S. PATENT DOCUMENTS 5,169,402 A    12/1992  Elloy
5,456,717 A *  10/1995  Zweymuller et al. ............ 623/8
5,665,090 A *   9/1997  Rockwood et al. ............ 606/80
5,755,811 A     5/1998  Tanamal et al.
2005/0075640 A1*  4/2005  Collazo et al. ................. 606/86

FOREIGN PATENT DOCUMENTS

| EP | 0135755 B1 | 2/1987 |
| EP | 0555613 B1 | 12/1996 |
| JP | 7-506038 A | 7/1995 |
| JP | 8-508175 A | 9/1996 |
| WO | WO94/12123 A1 | 6/1994 |
| WO | WO94/12124 A1 | 6/1994 |

* cited by examiner

*Primary Examiner*—Bruce E Snow
*Assistant Examiner*—Megan Wolf
(74) *Attorney, Agent, or Firm*—Baker & Daniels LLP

(57) ABSTRACT

The invention relates to an implant system having at least one shaft of a prosthesis, in particular a hip joint prosthesis, which can be anchored without cement, and a set of instruments for the preparation of the bone in which the shaft is to be anchored, wherein the shaft has an arcuate base body with a trapezoidal or rectangular cross-section and the set of instruments includes a first instrument which is shaped in accordance with the arcuate shape of the shaft and with which a recess serving for the reception of the base body can be established in the bone; and wherein the shaft is provided with ribs in the proximal region and the set of instruments includes a guide body shaped in accordance with the arcuate shape of the shaft for a second instrument with which structures can be manufactured in the bone serving to fix a path for the shaft ribs when the guide body is located in the recess.

15 Claims, 3 Drawing Sheets

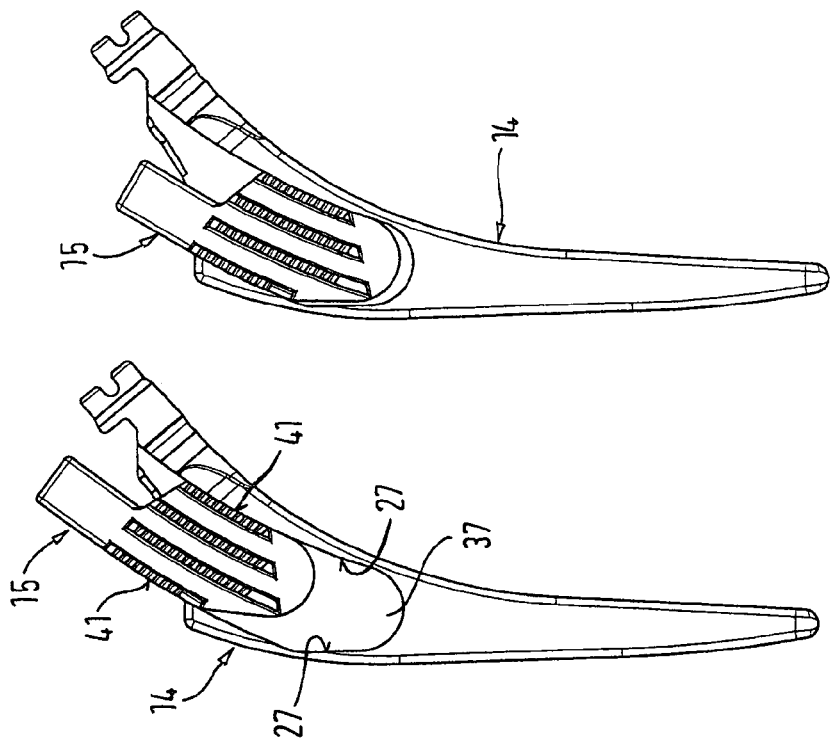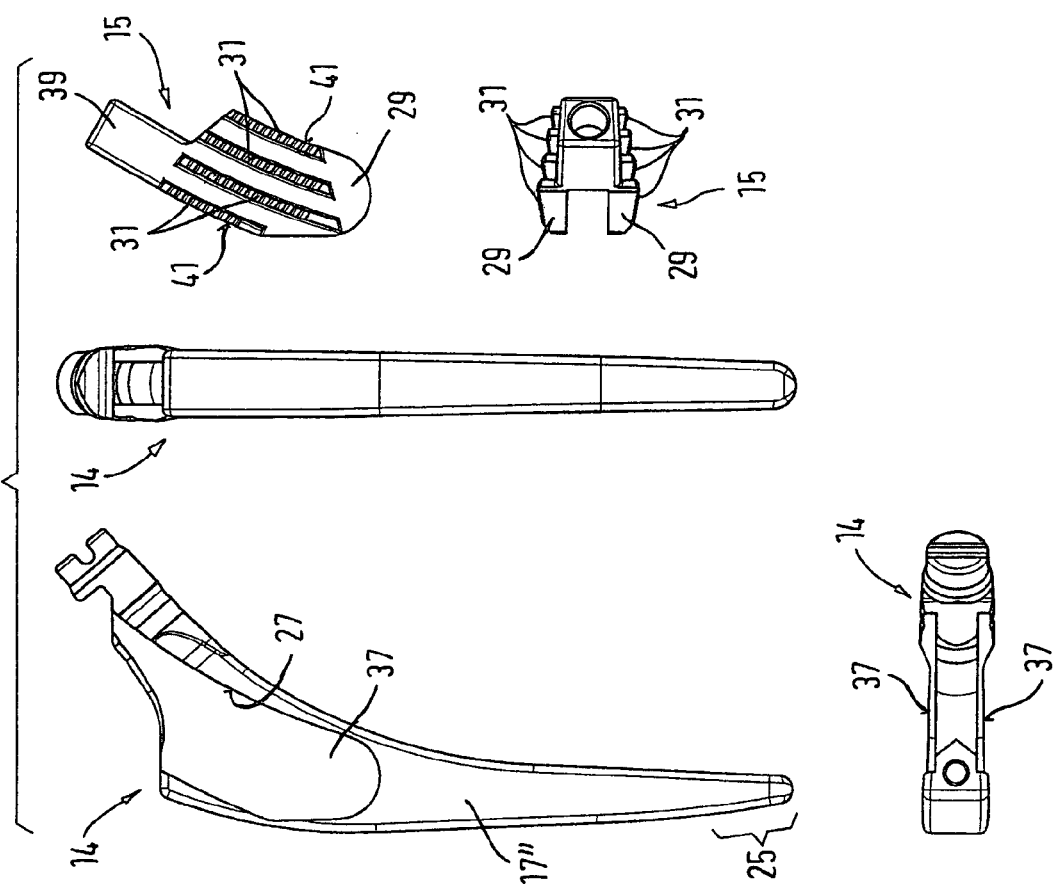

IMPLANT SYSTEM

Figure 1:
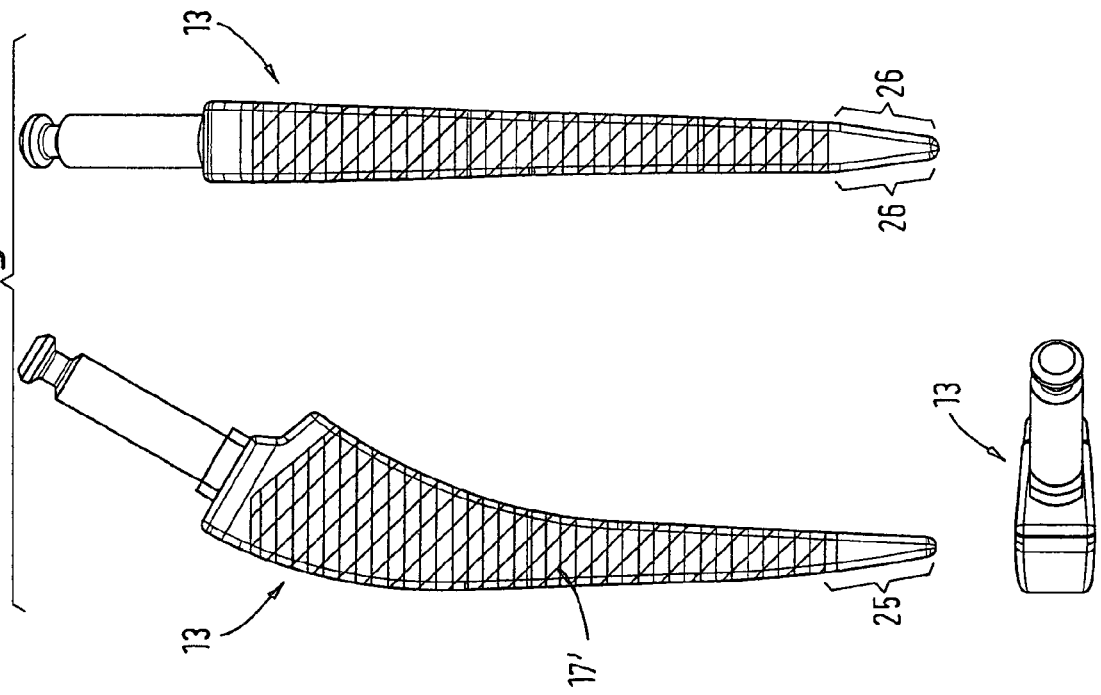

The invention relates to an implant system having at least one shaft of a prosthesis, in particular a hip joint prosthesis, which can be anchored without cement, and a set of instruments for the preparation of the bone in which the shaft is to be anchored.

A shaft of a hip joint prosthesis which can be anchored without cement is known from EP 0 135 755 A1. This prosthesis shaft is straight, has a trapezoidal cross-section and has groove-like recesses in the proximal region. The rib structure formed hereby is intended to improve the absorption of torsional forces in the proximal shaft region.

It is a problem on the insertion of straight shafts that the trochanter major of the femur can hereby be impaired. When curved shafts are used, in contrast, the trochanter can admittedly be maintained. However, the insertion of a curved shaft is again a problem if the shafts should have rib structures such as were mentioned above.

The reason for this is that the shaft can reach a pre-determined end position in the bone when hammered on a plurality of different movement paths. This is not a problem as long as the shaft has no rib structures. However, if the shaft is provided with rib structures, there is a risk that the ribs cut their own track into the bone which allows the shaft to move onto an incorrect path on which the shaft cannot be driven into the end position, at least no longer in the desired manner.

Due to these problems occurring on the insertion, curved shafts provided with ribs have not become as widespread as would have been expected due to the existing advantages per se of such shafts.

It is the object of the invention to provide an implant system with which curved prosthesis shafts can also be reliably anchored in the bone in a simple and reliable manner.

This object is satisfied by the features of claim 1 and in particular in that the shaft has an arcuate base body and the set of instruments includes a first instrument which is shaped in accordance with the arcuate shape of the shaft and with which a recess serving for the reception of the base body can be established in the bone, and wherein the shaft is provided with ribs in the proximal region and the set of instruments includes a guide body for a second instrument which is shaped in accordance with the arcuate shape of the shaft and with which second instrument structures can be established in the bone serving for the fixing of a path for the shaft ribs when the guide body is located in the recess.

In accordance with the invention, in addition to the instrument, in particular a rasp, serving for the establishment of the recess for the base body, a further instrument is provided with which the bone can be directly prepared for the guidance of the shaft ribs. The invention is characterized in that the recess previously established by means of the first instrument is used for the working to be carried out by the second instrument in that a guide body is used which is likewise shaped in accordance with the base body of the shaft, is inserted into the recess and then serves as a guidance for the second instrument. A path is subsequently fixed for the shaft ribs, and thus for the shaft overall, by means of the second instrument guided in a defined manner, said shaft subsequently being hammered to the bone working taking place by means of the second instrument.

Since a guide body corresponding to the shaft with respect to the arcuate form serves as a reference for the working movement of the second instrument, it can be ensured in accordance with the invention that a track is established for the shaft ribs and thus a path is pre-determined which is adapted to the arcuate shape of the base body of the shaft. It is hereby ensured that the curved shaft provided with the ribs moves in the desired manner into the end position previously pre-determined by means of the first instrument.

The ribs or the tangents at the ribs extend in accordance with the shaft curvature at an angle to the shaft axis different from zero. This rib angle in particular lies in the range from 0° to 45°, with, however, larger angles also being possible, and is selected in dependence on the arcuate shape of the shaft.

The guide body can be provided in the form of a separate part. Alternatively, the first instrument can simultaneously be made as the guide body for the second instrument. In this case, an additional guide body can be dispensed with.

Further preferred embodiments of the invention are also recited in the dependent claims, in the description and in the drawing.

Provision is thus preferably made for the cross-section of the shaft to be rectangular or trapezoidal with pronounced longitudinal edges which establish the contact to the cortex. Provision is preferably furthermore made for the arcuate shape of the base body to be selected in particular with respect to curvature and length in relation to two oppositely disposed edges, i.e. a lateral edge and a medial edge, such that an end position of the base body results which is clearly defined by a plurality of contact positions, in particular three contact positions, at the cortex of the bone. It is hereby ensured that the respective base body centers itself on insertion in accordance with its rectangular or trapezoidal cross-section and that hollow spaces are no longer present between the base body and the bone bed formed by the cortex in the end position since a clamping also takes place between the base body and the bone bed formed by the two lateral edges and between the two medial edges. The curvature of the base body and the length of the base body and/or the shaft are in particular matched to one another in a pre-determined manner.

It is particularly advantageous if, in accordance with a further embodiment of the invention, the extend of the shaft ribs is adapted to the arcuate shape of the base body of the shaft such that an end position of the base body clearly defined by a plurality of contact positions, in particular three contact positions, at the cortex of the bone can be reached between oppositely disposed lateral and medial edges. Provision is made for the contact positions not to be punctual, but to be formed in the form of zones stretched in the longitudinal direction.

The ribs of the shaft can extend in both a straight and in a curved manner. In this process, it is not compulsory for all ribs to be straight or for all ribs to be curved. Both straight and curved ribs can be provided within a rib structure including a plurality of ribs. It is basically also possible to provide only one single rib on each side of the shaft. It is further more possible that one or more ribs are only provided on one side.

The extent of the ribs can in particular be made dependent on their respective length. In this process, ribs not exceeding a specific length can be made straight, whereas ribs exceeding a specific length can extend in a curved manner.

Provision is furthermore preferably made for the shaft ribs to extend toward distal starting from an at least approximately common plane. This common plane is preferably disposed in the region of a resection plane of the bone with an inserted shaft.

If both straight and curved shaft ribs are present, provision is preferably made in accordance with a further embodiment of the invention for the straight shaft ribs, on the one hand, and tangents at the curved shaft ribs, on the other hand, to extend to the shaft axis at the same angle different from zero.

Provision can in particular be made with a relatively long shaft for its base body to be provided with a flattened area at its lateral side in the region of its distal end. This preferably also applies to the first instrument and to the guide body. The observation of an optimum path on the hammering in of the shaft or on the insertion of the first instrument and of the guide body is hereby facilitated. The distal tip can in each case be displaced asymmetrically toward medial.

It is furthermore proposed that the first instrument is provided with a respective chamfer at the anterior and posterior sides.

Provision can furthermore be made for the distal end of the first instrument to project in the distal direction beyond a base body of the first instrument corresponding to the base body of the shaft. The first instrument is hereby provided with a distal extension in comparison with the shaft.

The second instrument, with which the structures serving for the fixing of a path for the shaft ribs are established in the bone, is preferably movable toward distal along a guide path pre-determined by the guide body.

This guide path and the shaft ribs are adapted to one another with respect to their extent so that the shaft ribs run in their own, pre-determined track on the hammering in of the shaft. The guide path is preferably curved in accordance with shaft ribs extending in a curved manner.

The guide provided at the guide body for the second instrument is furthermore preferably made as a compulsory guide in full or regionally.

Provision is furthermore preferably made for the second instrument to be U-shaped or fork-shaped and for it to be pushable onto the guide body with the free ends of the U arms or fork arms at the front.

It is furthermore proposed in accordance with the invention that the second instrument is provided on its front side and/or rear side with a number of working webs corresponding to the number of shaft ribs. The working webs are matched to the geometry of the shaft ribs and are preferably made in each case as chisels or rasps.

Consequently, an at least partial negative of the shaft region provided with the ribs can be established using the second instrument, whereby the ribs are forced onto the correct path right from the start on the hammering in of the shaft.

The working webs can each be shorter and/or lower than the corresponding shaft ribs. The track length which can hereby be established in dependence on the length of the guide formed at that guide body for the second instrument is sufficient for a clear track formation in the bone.

Provision is furthermore preferably made for all working webs to have at least substantially the same length.

Figure 2:
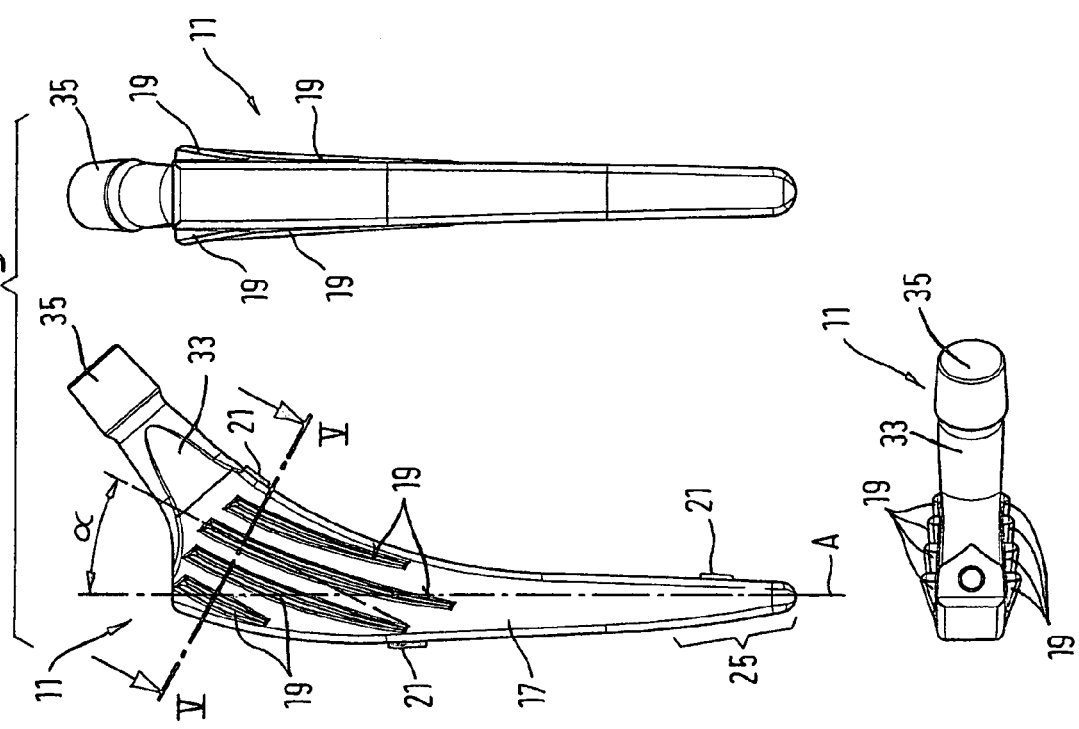
Figure 5:
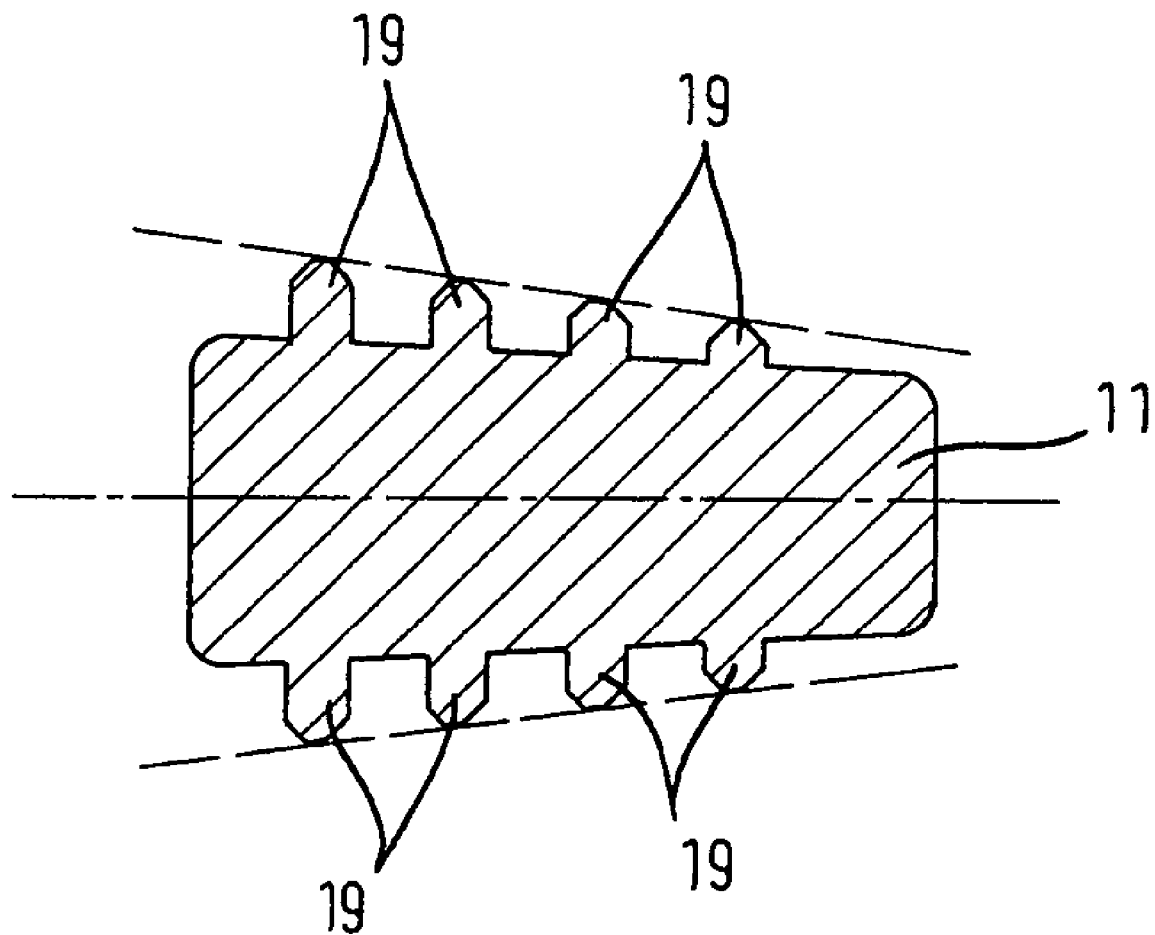

The invention will be described in the following by way of example with reference to the drawing. There are shown:

FIG. 1 different views of a shaft in accordance with an embodiment of the invention;

FIG. 2 different views of a first tool in accordance with an embodiment of the invention made as a rasp;

FIG. 3 different views of a guide body and of a second tool in accordance with an embodiment of the invention couplable to the guide body and made as a chisel or as a rasp;

FIG. 4 the guide body and the second tool of FIG. 3 in the coupled state in different relative positions; and FIG. 5 a cross-section in the curved proximal part of the shaft of FIG. 1 in an enlarged representation.

The shaft 11 of a hip joint prosthesis in accordance with the invention shown in FIG. 1 has a base body 17 curved in arcuate shape, a neck 33 and a coupling section 35 for a head of a prosthesis (not shown). The arcuate shape of the base body 17 is of a design opening conically in the direction of the axis of the neck.

The base body 17 has a rectangular or trapezoidal cross-section with pronounced edges in its longitudinal direction.

Four respective ribs 19 extending in parallel and of different length are applied in the proximal region of the base body 17 on the front side and on the rear side of the shaft 11 and extend toward distal starting from an approximately common plane. This plane is selected such that it lies in the region of the resection plane of the bone with the shaft 11 inserted in the bone (not shown).

Starting from this plane, the ribs 19 each extend in a straight manner, with in each case a slightly curved rib section with a constant radius of curvature adjoining with the longer ribs 19, with the respective proximal straight rib section coinciding with the tangent at the curved rib section.

The straight rib sections and thus the tangents at the curved rib sections extend toward the shaft axis A at an angle α different to zero.

The height of the ribs 19 reduces toward distal. As can in particular be seen from the lower representation in FIG. 1, the ribs 19 each have a rectangular base with a top triangle in cross-section, i.e. the ribs 19 extend upwardly to a tip.

The arcuate shape of the base body 17 is selected such that the respectively oppositely disposed lateral and medial edges of the base body 17 lie on the cortex of the bone forming the bone bed for the base body 17 at three contact positions 21 at the desired end position of the shaft 11 in the bone. This ensures that the base body 17 always wedges in the same end position in the bone at which there are no longer any hollow spaces present between the base body 17 and the bone bed and the base body 17 centers itself on the hammering in of the shaft 11.

In the region of its distal end, the base body 17 is provided at its lateral side with a flattened area 25. The hammering in of the shaft 11 along the desired path is hereby facilitated.

The rasp 13 in accordance with the invention shown in FIG. 2 forming the first instrument in the sense of the invention is characterized in that it has a base body 17' which corresponds to the base body 17 of the shaft 11 with respect to the arcuate shape. The rasp 13 serves to prepare the medullary cavity of the bone and/or the cortex such that the shaft 11 can be wedged in the desired end position by being hammered in.

The distal end of the rasp 13 projects beyond the base body 17' in the distal direction and forms a tip which is provide with a respective chamfer 26 on the ventral and dorsal sides to take account of the curvature of the femoral bone and to permit the use of the instrument for the left femur and for the right femur. In this process, the tip of the rasp is orientated more to medial to be able to be centered better during the whole lowering procedure.

The guide body 14 in accordance with the invention shown in FIG. 3 is also adapted to the shaft 11 to the extent that it has a base body 17" which corresponds to the base body 17 of the shaft 11 with respect to the arcuate shape. The end positions of the shaft 11 and of the guide body 14 are hereby identical so that the second instrument 15, which is likewise shown in FIG. 3 and which will be looked at in more detail in the following, can be guided along the guide body 14 such that structures are hereby established in the bone where subsequently the shaft 11 is guided by its ribs 19 on the hammering in.

Consequently, a path can be pre-determined for the shaft ribs 19 in the bone by means of the guide body 14 and of the second instrument 15 guided at the guide body 14, with the base body 17 of the shaft 11 moving into the desired end position on said path.

In the embodiment shown, the guide body 14 is provided at its front side and at its rear side with recessed flat sides 37 which are bounded by side walls serving as guide surfaces 27. The curvature of the guide surfaces 27 is selected in accordance with the curvature of the shaft ribs 19 such that the shaft ribs 19 run in their own track on the hammering in of the shaft 11.

The second instrument 15 is made in U shape or in fork shape and includes two arms 29 connected to one another by a coupling section 39, with the spacing between the arms 29 being selected in accordance with the thickness of the guide body 14 in the region of the flat sides 37.

As FIG. 4 shows, the second instrument 15 can be pressed onto the proximal region of the guide body 14 provided with the flat sides 37 and can be pushed along the guide body 14 like a slide, and indeed on a path which is pre-determined by the guide surfaces 27 cooperating with corresponding counter-surfaces 41 of the second instrument 15 (FIG. 3).

The guide arms 29 of the second instrument 15 are provided at their outsides with working webs 31 formed in each case as chisels or as rasps. The working webs 31 are arranged in accordance with the ribs 19 of the of the shaft 11, with the curvature of the working webs 31 moreover corresponding to the curvature of the shaft ribs 19.

In a surgical procedure carried out by means of the implant system in accordance with the invention, as was explained above, a recess serving for the reception of the shaft 11 (FIG. 1) is first established in the bone using the rasp 13 (FIG. 2) in that the medullary cavity and the cortex are worked accordingly. Due to the arcuate shape provided for the implant system in accordance with the invention, the trochanter major of the femur is not impaired, since the preparation and the anchoring take place through the resection surfaces of the start of the neck of the bone.

Subsequently, after removal of the rasp 13, the guide body 14 (FIG. 3) is inserted into the recess previously established by means of the rasp 13. In this process, the base body 17" of the guide body 14 which corresponds to the base body 17 of the shaft 11 with respect to its arcuate shape is brought into the same end position as later the shaft 11.

The second instrument 15 (FIG. 3) is then placed onto the compulsory guide formed on the guide body 14 by the guide surfaces 27. By moving the second instrument 15 relative to the guide body 14 along the path pre-determined by the compulsory guide, tracks are established in the bone for the ribs 19 by means of the working webs 31.

After removal of the guide body 14 and of the second instrument 15, the shaft 11 is finally hammered in. In this process, the shaft ribs 19 run in the tracks which have previously been established by means of the second instrument 15 and which force the shaft 11 onto a secure path on which the shaft 11 reaches its end position previously pre-determined by means of the rasp 13 guided by the ribs 19 in the desired manner.

REFERENCE NUMERAL LIST 11 shaft
13 first instrument, rasp
14 guide body
15 second instrument, chisel
17, 17', 17" base body
19 rib
21 contact position
25 flattened area
26 chamfer
27 guide surface
29 U or fork arm
31 working web
33 neck
35 coupling section
37 flat side
39 coupling section
41 counter surface
α rib angle
A shaft axis

The invention claimed is:

1. An implant system comprising:
   a prosthesis having a prosthesis body and an arcuate rib extending therefrom, said arcuate rib defining a first radius of curvature;
   a guide body dimensioned to correspond to a portion of said prosthesis, said guide body having an arcuate guide surface; and
   an instrument having a counter-surface corresponding to said guide surface of said guide body and a web extending from said instrument, said web corresponding to said arcuate rib of said prosthesis, said web having a radius of curvature substantially equal to said first radius of curvature of said rib, said counter-surface of said instrument and said guide surface of said guide body operable to repeatably couple said instrument to said guide body by arcuately passing said counter-surface along an arcuate path defined by said arcuate guide surface, wherein the position of said web relative to said guide body replicates the position of said rib of said prosthesis relative to said prosthesis body when said instrument is coupled to said guide body.

2. The implant system of claim 1, wherein said prosthesis comprises a long bone prosthesis.

3. The implant system of claim 1, wherein said prosthesis comprises a femoral prosthesis.

4. The implant system of claim 1, wherein said arcuate rib extends substantially in a direction of a longitudinal axis of the prothesis.

5. The implant system of claim 1, wherein said guide surface defines a second radius of curvature, said second radius of curvature substantially equal to said first radius of curvature.

6. The implant system of claim 1, wherein said instrument further comprises a substantially U-shape.

7. The implant system of claim 1, wherein said prosthesis further comprises a straight rib, said straight rib and a tangent of said arcuate rib extending toward a longitudinal axis of said prosthesis body at the substantially same angle.

8. The implant system of claim 1, wherein said arcuate rib extends outwardly from said prosthesis a first distance and said web extends outwardly from said instrument a second distance, wherein said second distance is less then said first distance.

9. An implant system comprising:
   a femoral prosthesis having a plurality of arcuate ribs extending therefrom, at least one of said plurality of arcuate ribs defining a first radius of curvature;
   a guide body dimensioned to correspond to said prosthesis, said guide body including an arcuate guide surface; and
   an instrument dimensioned for receipt on said guide body, said instrument having a counter-surface and a plurality of arcuate webs extending therefrom, said plurality of arcuate web corresponding to said plurality of arcuate ribs of said femoral prosthesis, at least one of said plurality of webs having a radius of curvature substantially equal to said first radius of curvature of said at least one of said plurality of ribs, said instrument repeatably coupleable to said guide body by arcuately passing said counter-surface along an arcuate path defined by said arcuate guide surface, wherein the position of said plurality of webs relative to said guide body replicates the position of said plurality of ribs relative to said femoral prosthesis when said instrument is coupled to said guide body.

10. The implant system of claim 9, wherein said prosthesis comprises a long bone prosthesis.

11. The implant system of claim 9, wherein said arcuate rib extends substantially in the direction of a longitudinal axis of the prosthesis.

12. The implant system of claim 9, wherein said guide surface of said guide body defines a recess, said instrument dimensioned for receipt at least partially within said recess.

13. The implant system of claim 12, wherein said guide surface defines a second radius of curvature, said second radius of curvature substantially equal to said first radius of curvature of said rib of said prosthesis.

14. The implant system of claim 9, wherein said prosthesis further comprises a straight rib, said straight rib and a tangent of said arcuate rib extending toward a longitudinal axis of said prosthesis body at the substantially same angle.

15. The implant system of claim 9, wherein said arcuate rib extends outwardly from said prosthesis a first distance and said web extends outwardly from said instrument a second distance, wherein said second distance is less then said first distance.

* * * * *